United States Patent
Kitagaito et al.

(10) Patent No.: US 8,625,252 B2
(45) Date of Patent: Jan. 7, 2014

(54) ION DIFFUSING APPARATUS AND ION GENERATING CARTRIDGE

(75) Inventors: Hiroshi Kitagaito, Osaka (JP); Takashi Kohama, Osaka (JP); Hiroyasu Yamashita, Osaka (JP); Haruhito Miyazaki, Osaka (JP); Jun Katayama, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 408 days.

(21) Appl. No.: 13/056,894

(22) PCT Filed: Aug. 27, 2009

(86) PCT No.: PCT/JP2009/064932
§ 371 (c)(1),
(2), (4) Date: Jan. 31, 2011

(87) PCT Pub. No.: WO2010/024318
PCT Pub. Date: Mar. 4, 2010

(65) Prior Publication Data
US 2011/0133098 A1 Jun. 9, 2011

(30) Foreign Application Priority Data
Aug. 28, 2008 (JP) ................. 2008-219848

(51) Int. Cl.
*H01T 23/00* (2006.01)
(52) U.S. Cl.
USPC ........................................ 361/230
(58) Field of Classification Search
None
See application file for complete search history.

(56) References Cited

U.S. PATENT DOCUMENTS

2007/0109711 A1 5/2007 Sekoguchi et al.
2009/0116162 A1 5/2009 Onezawa et al.

FOREIGN PATENT DOCUMENTS

| JP | 2004-363088 A | 12/2004 |
|---|---|---|
| JP | 2005-156027 A | 6/2005 |
| JP | 2006-170476 A | 6/2006 |
| JP | 2007-287368 A | 11/2007 |
| JP | 2007-335092 A | 12/2007 |
| JP | 2008-59795 A | 3/2008 |
| JP | 4114602 B2 | 7/2008 |
| JP | 2008-192556 A | 8/2008 |

OTHER PUBLICATIONS

JP 2008-059795 (Machine Translation) of Ion Generating Device, Kataoka Yashutaka, Mar. 2008.*

(Continued)

*Primary Examiner* — Jared Fureman
*Assistant Examiner* — Terrence Willoughby
(74) *Attorney, Agent, or Firm* — Birch, Stewart, Kolasch & Birch, LLP

(57) ABSTRACT

An ion diffusing apparatus is disclosed which can maintain a stable ion supplying capability. In the ion diffusing apparatus, the ion generator is detachable for easy maintenance and can deliver the positive ions and negative ions to a remote position while uniformly generating positive ions and negative ions. The ion diffusing apparatus includes an ion generator housing which houses the generator so that a positive ion generating part and a negative ion generating part are provided separately in a direction crossing a flow direction of a stream from a fan, and an ion generating surface is exposed which conforms to a stream flow surface of a stream flow passage extended from the fan to a supply opening. The ion generator may also be a cartridge which has an ion generating surface shaped to conform to the stream flow surface of the stream flow passage.

16 Claims, 5 Drawing Sheets

(56) References Cited

OTHER PUBLICATIONS

JP 2007-335092 (Machine Translation) of Ion Generating and Air Conditioning Device Equipped Therewith, Nishida Hiroshi, Dec. 2007.*

JP 2006-170476 (Machine Translation) of Ion Generator and Air Conditioner, Nishida et al.. Jun. 2006.*

JP 2005-156027 (Machine Translation) of Air Conditioner, Fan Heater and Method for Deactivating Antigenic Substance, Shimizu et al., Jun. 2005.*

International Search Report for PCT/JP2009/064932, mailed on Nov. 2, 2009.

\* cited by examiner

US 8,625,252 B2

ION DIFFUSING APPARATUS AND ION GENERATING CARTRIDGE

TECHNICAL FIELD

The present invention relates to an ion diffusing apparatus that includes an ion generator and a fan, more particularly, to an ion diffusing apparatus that facilitates replacement of the ion generator and is able to keep a stable ion supplying capability; and to an ion generating cartridge.

BACKGROUND ART

In recent years, a function is discovered, in which by means of positive ions and negative ions generated into the air, germs floating in the air are killed and viruses are inactivated; and products such as an air cleaner and the like to which this technology is applied are attracting attention from people.

Besides, as an ion generating portion that generates the positive ions and the negative ions, a plasma discharge type is known, in which electric discharge is performed between a needle-shape positive discharge electrode and a plate-shape induction electrode, and between a needle-shape negative discharge electrode and the plate-shape induction electrode; thus, the positive ions are generated from the positive discharge electrode and the negative ions are generated from the negative discharge electrode. The plasma discharge is performed at the needle-shape positive and negative discharge electrodes, so that the air and vapors are ionized and the positive ions and negative ions are generated. As the positive ion, $H^+(H_2O)_m$ (m is a natural number), in which a plurality of water molecules are bonding to a circumference of a hydrogen ion, is chiefly generated; and as the negative ion, $O_2^-(H_2O)_n$ (n is a natural number), in which a plurality of water molecules are bonding to a circumference of an oxygen ion, is chiefly generated.

If the above $H^+(H_2O)_m$ and $O_2^-(H_2O)_n$ bond to a surface of a floating germ, chemical reaction occurs, thereby generating hydrogen peroxide ($H_2O_2$) or hydroxyl radical (.OH) that are active species. Because of this, the floating germ is destroyed by the decomposition action of the active species. It is said that in this way, it is possible to kill or inactivate the germ-relatives in the air such as bacteria, viruses and the like to remove them.

As described above, by supplying $H^+(H_2O)_m$ and $O_2^-(H_2O)_n$ into a room at the same time, it becomes possible to kill and inactivate the germ-relatives contained in the air of the room. However, in a case where impurities or dust collects on the needle-shape discharge electrode that is the ion generating portion, the ion generation effect deteriorates, so that it becomes impossible to supply a desired amount of generated ions.

To kill and inactivate the germ-relatives in the air to remove them, because an amount of the positive ions and of the negative ions are needed, more than a predetermined amount of the positive ions and of the negative ions per unit volume becomes necessary, so that as for an ion generating portion whose ion generation effect deteriorates, it is preferable to eliminate the cause of the deterioration or repair the ion generating portion.

Because of this, to facilitate demounting, cleaning and maintenance of an air processing unit and an ion diffusing apparatus, an air processing unit and an ion diffusing apparatus which are removably mounted on a base portion for mounting the air processing unit and the ion diffusing apparatus are already proposed (e.g., see patent document 1).

CITATION LIST

Patent Literature

PLT1: Japanese patent No. 4114602B2

SUMMARY OF INVENTION

Technical Problem

By supplying the positive ions and negative ions into a room, it is possible to kill and inactivate germ-relatives floating in the air to clean the room; however, the germ-relatives are killed, inactivated and removed by using the positive ions and negative ions at the same time, it is preferable the amounts of positive ions and negative ions remaining in the air are equal to or more than a predetermined amount; and the amounts are approximately equal to each other.

Moreover, according to a method in which when diffusing, by means of a fan and the like, the positive and negative ions that are generated from an ion generating portion of an ion generating apparatus, the ions are diffused by means of an air flow generated by simply sending a wind to the ion generating portion, the positive and negative ions collide with each other to be neutralized, so that it is hard to evenly disperse the ions into the air without the neutralization. Besides, according to a method in which the positive and negative ions are separately generated and carried by means of a sending wind, it is possible to carry the ions to a distant place by preventing the ions from colliding with each other; however, the amount of the dispersed positive and negative ions does not become even, so that it is impossible to achieve desired killing and inactivating effects.

Because of this, an ion diffusion apparatus is desired, in which the positive and negative ions are evenly generated; the remaining amount per unit volume of the ions sent out into a room is increased, and the percentages of the respective positive- and negative-ion remaining amounts are substantially the same as each other. Moreover, a structure which facilitates the maintenance of the ion generating portion is desired.

In light of the above problems, it is an object of the present invention to provide an ion diffusing apparatus and an ion generating cartridge which are so structured as to allow an ion generating apparatus to be freely mounted and demounted; able to generate evenly the positive ions and the negative ions while sending out them far into a room.

Solution to Problem

To achieve the above object, an ion diffusing apparatus according to the present invention that diffuses positive ions and negative ions generated by plasma discharge into a room, the ion diffusing apparatus comprises:

a fan that generates an air flow for exhaling air, which is inhaled from an inlet, from an outlet into the room via a flow passage that is formed in the apparatus;

an ion generating apparatus that includes a positive ion generating portion and a negative ion generating portion; and supplies positive ions generated from the positive ion generating portion and negative ions generated from the negative ion generating portion into the air flowing through the flow passage; and an ion generating apparatus housing portion that houses the ion generating apparatus in such a posture that an ion generating surface of the ion generating apparatus is exposed with the ion generating surface matched with a flow surface of one surface which forms a wall surface of the flow passage; wherein the ion generating apparatus is able to be inserted and pulled out from an insertion opening that is formed through a side of the outlet, and freely mountable and demountable into and from the ion generating apparatus housing portion.

According to this structure, the ion generating apparatus, whose ion generating surface is exposed in such a posture that the ion generating surface matches with the flow surface of the flow passage, and which is freely mountable and demountable into and from the ion generating apparatus housing portion, is disposed, so that it is possible to obtain the ion diffusing apparatus, in which the maintenance is easy and it becomes possible to exhale the ions emitted from the ion generating surface by means of a streamline flow along the flow surface, and to send out the positive ions and the negative ions far into the room by curbing the collision between the positive ions and the negative ions and preventing them from being neutralized.

Besides, in the ion diffusing apparatus having the above structure according to the present invention, the one surface is composed of a lower lateral wind-direction plate that forms a lower wall surface of the flow passage. According to this structure, it is possible to obtain the ion diffusing apparatus that sends out the positive and negative ions in a horizontal direction of the room along a flow surface of the lower lateral wind-direction plate; and it becomes possible to exhale the positive and negative ions into the room region where people are living.

Besides, the ion diffusing apparatus having the above structure according to the present invention is formed as an ion generating cartridge that includes an ion generator that has the positive ion generating portion and the negative ion generating portion, the ion generating cartridge houses the ion generator and unitarily includes:

an insertion guide portion;

a position guide portion; and a lever member that engages with an engagement portion disposed in the ion generating apparatus housing portion of the apparatus main body to fix the position of the cartridge;

wherein a structure is employed, in which the ion generating apparatus is inserted from the insertion opening into the ion generating apparatus housing portion via the insertion guide portion and the position guide portion; and fixes the ion generating apparatus in such a posture that the ion generating surface is matched with the flow passage via the position guide portion and the lever member.

According to this structure, the ion generating apparatus is formed as the cartridge type that unitarily includes: the insertion guide portion; the position guide portion; and the lever member, so that the ion generating apparatus which facilitates the maintenance is obtained. Besides, it is possible to fix the ion generating surface while exposing the ion generating surface, which has the curved surface matching with the flow surface of the lower wind-direction plate, via a cut-away portion formed through the lower wind-direction plate.

Besides, in the ion diffusing apparatus having the above structure according to the present invention, the ion generating apparatus includes the ion generator in which the positive ion generating portion and the negative ion generating portion are spaced apart in a direction that intersects an air flow direction; and a vertical wind-direction plate, which partitions the flow passage into flow passages for the respective positive ion generating portion and negative ion generating portion, is disposed in the flow passage. According to this structure, it becomes possible to separately carry the positive ions and the negative ions, so that it is possible to curb further effectively the collision between both ions of the positive and negative ions; and to obtain the ion diffusing apparatus that is able to send out the ions far into the room without neutralizing the ions.

Besides, in the ion diffusing apparatus having the above structure according to the present invention, an intermediate lateral wind-direction plate, which partitions a flow passage between the lower lateral wind-direction plate and an upper lateral wind-direction plate that forms an upper wall surface of the flow passage, is disposed to partition the flow passage that extends from the fan to the outlet into multi-stage streamline flow passages;

a plurality of the ion generating apparatuses are disposed in parallel with each other to form a continuous-length ion generating surface that has alternately the positive ion generating portion and the negative ion generating portion in a line at a predetermined pitch along the flow passage of the lower lateral wind-direction plate; and the vertical wind-direction plate, which partitions the flow passage into the flow passages for the respective positive ion generating portion and negative ion generating portion, is so disposed as to penetrate the multi-stage streamline flow passages.

According to this structure, each ion generating apparatus, which includes the positive ion generating portion and the negative ion generating potion, becomes freely mountable and demountable, so that not only the maintenance becomes easy but also sophisticated maintenance becomes possible. Besides, the flow passage is disposed for every electrode, so that it becomes possible to send out the positive and negative ions far into the room by curbing the neutralization of the positive and negative ions.

Besides, in the ion diffusing apparatus having the above structure according to the present invention, the vertical wind-direction plate is angled in such a way that the ions are exhaled at a wide angle with respect to a width direction in which the ion generating apparatuses are disposed in parallel with each other. According to this structure, the flow passage disposed for every ion generating portion is widened in a wide angle, so that it is possible to disperse the ions into a predetermined area of the room.

Besides, in the ion diffusing apparatus having the above structure according to the present invention, the ion generating cartridge includes:

an input-output connector portion that connects with an external electrode to perform input and output;

a control board that controls driving of the positive ion generating portion and the negative ion generating portion by means of electric power obtained via the input-output connector portion; and an ion sensor that detects the ions generated by the ion generating portion.

According to this structure, it is possible to obtain the ion generating apparatus formed as the ion generating cartridge which is able to be connected to an external power supply or an external terminal via the input-output connector portion and is easy to check for normal operation via the ion sensor that is disposed in advance.

Besides, in the ion diffusing apparatus having the above structure according to the present invention, the ion sensor is a negative ion detection sensor that is disposed on a downwind side with respect to the negative ion generating portion of the ion generating cartridge. According to this structure, the amount of negative ions generated from the negative ion generating portion during an operation time of the ion diffusing apparatus is detected, so that it is possible to detect whether the ion generating cartridge is normally operating or not and how much the ion generating cartridge deteriorates.

Besides, in the ion diffusing apparatus having the above structure according to the present invention, a positive ion generating electrode of the positive ion generating portion of the ion generator and a negative ion generating electrode of the negative ion generating portion of the ion generator are each of a double electrode type in which two generating electrodes are disposed close to each other. According to this structure, it is possible to increase the amount of generated ions.

Besides, in the ion diffusing apparatus having the above structure according to the present invention, the ion generating cartridge is formed as a two-stage ion generating type in which the ion generators are disposed in two stages and in parallel with each other; and positive and negative polarities of the positive ion generating electrode and the negative ion generating electrode of the respective ion generators are disposed at reversed positions. According to this structure, it becomes possible to exhale the positive ions and the negative ions into the same flow passage by driving the two-stage ion generators at the same time; and to alternately exhale the positive ions and the negative ions into the same flow passage by alternately driving the two-stage ion generators.

Besides, in the ion diffusing apparatus having the above structure according to the present invention, the ion generators in the respective stages of the ion generating cartridge of the two-stage ion generating type are alternately operated. According to this structure, it is possible to prolong double the life of the ion generating cartridge.

Besides, in the ion diffusing apparatus having the above structure according to the present invention, an open-close cover for closing and opening the insertion opening is disposed; the ion generating cartridge is inserted until a predetermined position; when the lever member is rotated to a fix lock position where a hook portion of the lever member is engaged with the engagement portion of the main body, the closing of the open-close cover is possible; and in a state in which the lever member is not rotated to the fix lock position, the lever member hinders the open-close cover from being closed. According to this structure, in a case where the ion generating cartridge is not disposed at a correct position of the ion generating apparatus housing portion and not locked, it is impossible to close the open-close cover, so that it is possible to easily detect the faulty disposition of the ion generating cartridge.

Besides, in the ion diffusing apparatus having the above structure according to the present invention, a drive start-stop operation portion is disposed on the apparatus main body; the operation portion is provided with: a drive mode set portion that sets a rotation speed of the fan; a cartridge disposition time set portion that sets disposition of a new ion generating cartridge; a timer set portion; a replacement recommendation indication portion that recommends cartridge replacement after elapse of a predetermined time after the new cartridge is disposed and the operation is started; and a level indication portion that indicates whether the amount of the ions generated by each ion generating cartridge is equal to, over or under a predetermined amount. According to this structure, as for an ion generating cartridge whose service life is decided in advance, it is possible to notify that a replacement time is coming by performing indication for recommending the replacement after elapse of a time from the disposition of the new cartridge. Besides, if the amount of generated ions is equal to or under the predetermined amount, the information is indicated, so that it is possible to know the maintenance is necessary.

Moreover, the ion generating apparatus according to the present invention, which generates the positive ions and negative ions by means of the plasma discharge, is formed as an ion generating cartridge that includes:

an input-output connector portion that connects with an external electrode and performs input and output of a signal;

an ion generator in which a positive ion generating electrode and a negative ion generating electrode are disposed;

an ion sensor that detects ions generated by the ion generator; and a control board that controls drive of the ion generator by means of electric power obtained via the input-output connector portion.

According to this structure, the respective ion generating portions for the positive ions and the negative ions are disposed, so that it becomes easy to handle the ion generating apparatus of the cartridge type that generates the positive and negative ions at the same time. Besides, the ion sensor is disposed, so that it is possible to obtain the ion generating cartridge which is easy to check for normal operation.

Besides, in the ion generating cartridge having the above structure according to the present invention, the ion sensor is a negative ion detection sensor that detects the negative ions generated from the negative ion generating electrode. According to this structure, when the ion generating electrode portion deteriorates, the amount of the negative ions generated from the negative ion generating electrode also decreases, so that by detecting the amount of the negative ions generated from the negative ion generating electrode during the operation, it is possible to detect whether the ion generating cartridge is normally operating or not and how much the ion generating cartridge deteriorates.

Besides, the ion generating cartridge having the above structure according to the present invention includes:

a lever member which has: a handle portion that is held at times of insertion and pulling-out of the cartridge; and a hook member that fixes the cartridge at a predetermined position after the insertion; wherein a side portion of a frame body of the cartridge is provided with: a guide protrusion portion, a butt surface and a guide surface that perform a guide function at the time of inserting the cartridge. According to this structure, it is possible to obtain the ion generating cartridge that becomes easily mountable and demountable at the predetermined position of the ion diffusing apparatus via the butt surface, the guide surface that perform the guide function and the lever member that includes the hook member.

Besides, the ion generating cartridge having the above structure according to the present invention has a rectangular shape when viewing an ion generating surface, from top, on which the positive and negative ion generating portions are disposed;

the ion generator is formed as a two-stage ion generating type in which positive and negative polarities of the ion generating electrode portions are disposed at reversed positions in two stages and in parallel with each other; and the ion generating surface is formed into a curved surface that matches with a flow surface where the ion generating cartridge is disposed.

According to this structure, the flow surface where the ion generating cartridge is disposed is provided with the rectangular-shape cut-away portion, so that it is possible to obtain the ion generating cartridge which is able to be disposed with the ion generating surface matched with the flow surface.

Besides, it becomes possible to send out the positive and negative ions into the partitioned flow passages at the same time and to alternately send out them.

Besides, in the ion generating cartridge having the above structure according to the present invention, the ion generators in the respective stages of the ion generating cartridge of the two-stage ion generating type are alternately operated. According to this structure, it is possible to obtain the ion generating cartridge which alternately sends out the positive and negative ions into the partitioned flow passages and the life of which becomes double.

Advantageous Effects of Invention

According to the present invention, the ion generating apparatus is obtained, in which while the ion generating surface is matched with the flow surface of the flow passage that extends from the fan to the outlet, the ion generating apparatus supplies the positive ions and the negative ions into the air flowing through the flow passage, and is freely mountable and demountable into and from the ion generating apparatus housing portion, so that it is possible to obtain the ion diffusing apparatus whose maintenance is easy and which is able to send out the positive ions and the negative ions far into a room by curbing the collision between the positive ions and the negative ions and without neutralizing them. Besides, the ion generating apparatus is formed as the ion generating cartridge that includes: the input-output connector; the ion generators for respectively generating the positive ions and the negative ions; the ion sensor; and the control board, so that it becomes easy to handle the ion generating apparatus of the cartridge type which generates the positive and negative ions at the same time and evenly. Besides, the ion sensor is disposed, so that it is possible to obtain the ion generating cartridge which is easy to check for normal operation.

BRIEF DESCRIPTION OF DRAWINGS

FIG. 1 (b) is a front view.

FIG. 2 (b) is a side sectional view showing a state in which the insertion is being performed; and FIG. 2 (c) is a side sectional view showing a state in which the insertion is completed.

FIG. 3 (b) is a plan view of an entire lever member.

FIG. 4 (b) is a side view.

DESCRIPTION OF EMBODIMENTS

Hereinafter, embodiments of the present invention are described with reference to the drawings. Besides, the same constituent members are indicated by the same reference numbers and detailed description of them is suitably skipped.

Figure 1A:
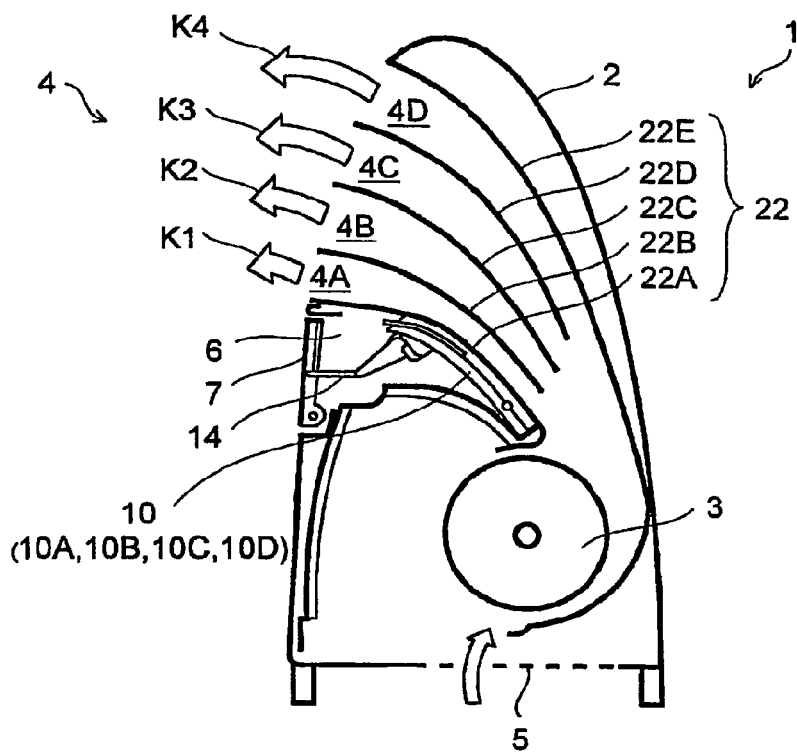
FIG. 1 shows an example of an ion diffusing apparatus according to the present invention, of which FIG. 1 (a) is a side sectional view.
Figure 1B:
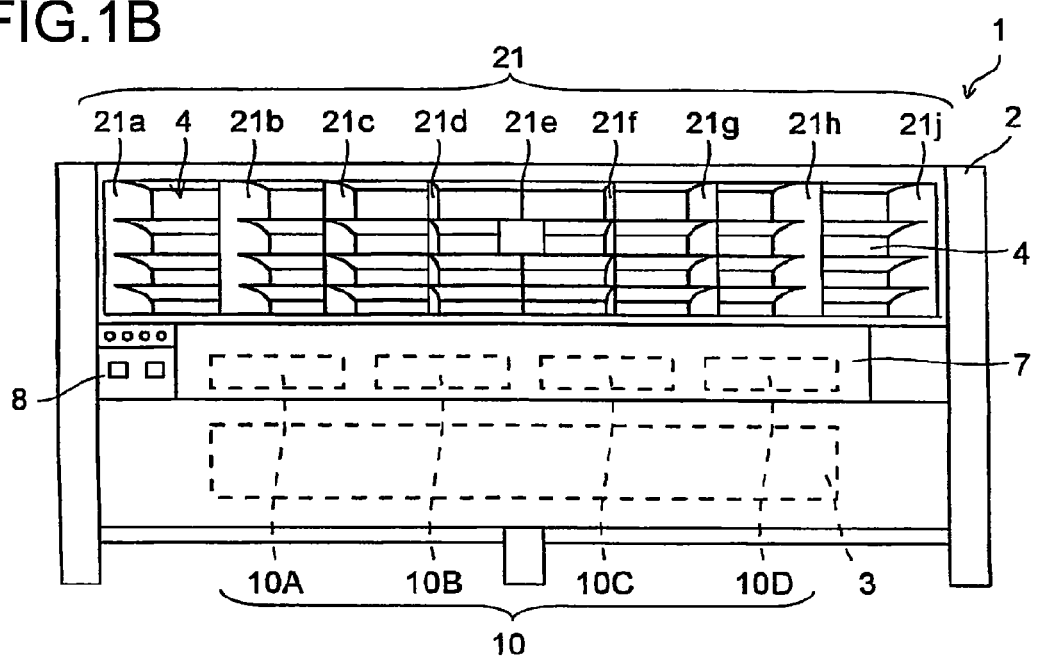

An ion diffusing apparatus according to the present embodiment is an ion diffusing apparatus that includes an ion generating apparatus and a fan, and sends out ions generated by the ion generating apparatus into a room; as shown in FIG. 1 (a), an apparatus main body 2 is provided with a fan 3 and an ion generating apparatus 10 that includes an ion generator which has a positive ion generating portion and a negative ion generating portion. Besides, an outlet 4 for sending out the ions generated by the ion generating apparatus 10 to outside is disposed on a front side of the apparatus main body 2; and an inlet 5 is disposed on another side (e.g., bottom surface) of the apparatus main body 2.

It is also possible to dispose an air filter at the inlet 5 that inhales air; and a stricture is employed, in which the air inhaled from the inlet 5 is sent to the ion generating apparatus 10 that performs plasma discharge via the fan 3; and the air and vapors are ionized and sent out from the outlet 4.

The ion generating apparatus 10 includes the ion generator that includes a pair of electrodes each of which performs the plasma discharge; as described later, a positive ion generating portion that includes a positive ion generating electrode and a negative ion generating portion that includes a negative ion generating electrode are disposed away from each other by a predetermined distance.

Besides, a lower lateral wind-direction plate 22A that serves as a lower wall surface of a flow passage which extends from the fan 3 to the outlet 4, and an upper lateral wind-direction plate 22E that serves as an upper wall surface of the flow passage which extends from the fan 3 to the outlet 4 are disposed. And, an ion generating apparatus housing portion, in which the ion generating apparatus 10 is disposed while an ion generating surface where the ion generator is disposed is matched with a flow surface of the lower lateral wind-direction plate 22A, is formed. Besides, an insertion opening 6 is formed on the outlet side to make it possible to freely mount and demount the ion generating apparatus 10 from the front side of the ion diffusing apparatus 1. Here, if a structure is employed, in which the ion generating apparatus 10 is formed as a cartridge type and disposed in the ion generating apparatus housing portion that is formed in the apparatus main body, the ion generating apparatus becomes freely mountable and demountable and the replacement becomes easy, which is preferable. Because of this, in the present embodiment, the ion generating apparatus 10 is formed as the cartridge type that unitarily includes: an insertion guide portion; a position guide portion; and a lever member 14 that engages with an engagement portion disposed in the ion generating apparatus housing portion of the apparatus main body to fix the position of the cartridge, so that a structure is obtained, in which the cartridge is freely mountable and demountable in such a posture that the ion generating surface is exposed to the flow surface via the lever member 14.

The ion generating apparatus 10 is formed as the cartridge type and freely mountable and demountable in a state in which the ion generating surface is matched with the flow surface that forms the flow passage; accordingly, it is preferable that the ion generating surface, where the positive ion generating portion and the negative ion generating portion are disposed, has a shape that matches with the flow surface. Besides, it is preferable that the positive and negative ion generating portions are disposed away from each other in a direction which intersects a flow direction. According to this structure, it becomes possible to send out the ions emitted from the ion generating surface by means of a streamline flow along the flow surface. Moreover, the positive and negative ion generating portions are disposed in the direction that intersects the flow direction, so that it becomes possible to send out the positive ions and the negative ions far into the room by curbing the collision between the positive ions and the negative ions and by preventing them from being neutralized.

Because of this, in a case where the flow passage that extends from the fan 3 to the outlet 4 has a bent shape, it is preferable that the ion generating surface of the ion generating apparatus 10 is formed into a curved surface which matches with the flow surface of the lower lateral wind-direction plate 22A that is bent.

Besides, the ion generating apparatus 10 of the cartridge type, which unitarily includes: the insertion guide portion; the position guide portion; and the lever member 14 that engages with the engagement portion disposed in the ion generating apparatus housing portion of the main body to fix the position of the cartridge, is inserted from the insertion opening 6 formed through the front surface of the apparatus and disposed, from outside of the flow passage, in such posture that the ion generating surface is exposed to the flow surface, so that the ion generating surface matches with the flow surface and it is possible to supply the ions into the air flowing through the flow passage without disturbing the air flow.

Because of this, along the streamline flow on the flow surface of the flow passage, it becomes possible to send out the positive and negative ions generated by the positive and negative ion generating portions disposed on the ion generating surface without disturbing the ions. Besides, the ion generating apparatus housing portion is formed under the lower lateral wind-direction plate 22A that forms the lower wall surface of the flow passage, so that it becomes possible to stably send out the positive and negative ions in a horizontal direction by means of the streamline flow formed on the lower wall surface.

To partition the flow passage extending from the fan 3 to the outlet 6 into streamline flow passages in a vertical direction, in the present embodiment, as shown in FIG. 1, between the lower lateral wind-direction plate 22A and the upper lateral wind-direction plate 22E, a second lateral wind-direction plate 22B, a third lateral wind-direction plate 22C and a fourth lateral wind-direction plate 22D are disposed as intermediate wind-direction plates; and by disposing these lateral wind-direction plates 22 (22A to 22E), the flow passage is partitioned into multi-stage streamline flow passages from an inner circumferential surface close to the fan 3 to an outer circumferential surface.

In the case of the above structure, the ion generating apparatus housing portion is formed in the apparatus main body and under the flow passage along the lower lateral wind-direction plate 22A, so that it is possible to insert the ion generating apparatus 10 of the cartridge type from the insertion opening 6 formed under the outlet 4, and freely mount and demount the ion generating apparatus 10, via an outer side of the lower lateral wind-direction plate 22A, in such posture that the ion generating surface is exposed to the flow surface.

Besides, to dispose the ion generating apparatus 10 with the ion generating surface matched with the flow surface of the lateral wind-direction plate 22, the ion generating surface may be used as part of the flow surface of the lateral wind-direction plate 22, which is able to be achieved by disposing the ion generating apparatus 10 in parallel with the lateral wind-direction plate 22; or by cutting away part of the flow surface of the lateral wind-direction plate 22 and disposing the ion generating apparatus 10. Accordingly, in the present embodiment, a structure is employed, in which the lower wind-direction plate 22 is provided with a cut-away portion 22a (see FIG. 2 (a)) for exposing the ion generating surface; and the ion generating surface of the ion generating apparatus 10 is exposed via the cut-away portion.

The ion generating apparatus 10 is so structured as to include the pair of the positive ion generating electrode and the negative ion generating electrode each of which performs the plasma discharge; accordingly, to make it possible to evenly send out the positive ions and the negative ions far into the room, it is preferable to carry the generated positive ions and negative ions by means of separate flow passages to prevent the ions from colliding with each other and being neutralized.

Besides, to mingle the positive ions and the negative ions in the room, the positive and negative ion generating portions may be so disposed as to be successively alternately disposed; by disposing the ion generators that have the pair of positive and negative electrodes in a line at a predetermined pitch, it is possible to alternately dispose the positive ion generating portions and the negative ion generating portions. Besides, the positive and negative ion generating portions are disposed away from each other by the predetermined distance, so that it is possible to curb the collision between the positive and negative ions at a time immediately after the generation of the ions.

Because of this, as shown in FIG. 1 (b), the ion diffusing apparatus 1 is so structured as to have the apparatus main body 2 that is laterally long; and in the inside of the main body 2, a plurality of the ion generating apparatuses 10 (10A, 10B, 10C, 10D) are disposed. Besides, to send out the ions generated from these ion generating apparatuses, the laterally long fan 3 is used to send out the ions from the laterally long outlet 4.

In disposing laterally the plurality of ion generating apparatuses 10 (10A, 10B, 10C, 10D) in parallel with each other, by disposing the ion generating apparatuses 10 that have the positive ion generating portion and the negative ion generating portion in a line and in parallel with each other, it is possible to alternately dispose the positive ion generating portion and the negative ion generating portion. Besides, the positive ion generating portion and the negative ion generating portion are alternately disposed; accordingly, vertical wind-direction plates 21 (21a to 21j) for partitioning the flow passage into flow passages for the respective ion generating portions are disposed; and the ions are sent out by means of the respective flow passages.

Besides, it is possible to angle each of the vertical wind-direction plates to exhale the ions into the room across a wide angle. For example, the angle of a central wind-direction plate 21d is set at 0°, and the angle is so set as to gradually become wider toward the sides, and the angles of the vertical wind-direction plates 21a, 21j at both ends are set at large angles facing outside, so that it is possible to exhale and diffuse the ions into the room across the wide angle.

Figure 5:
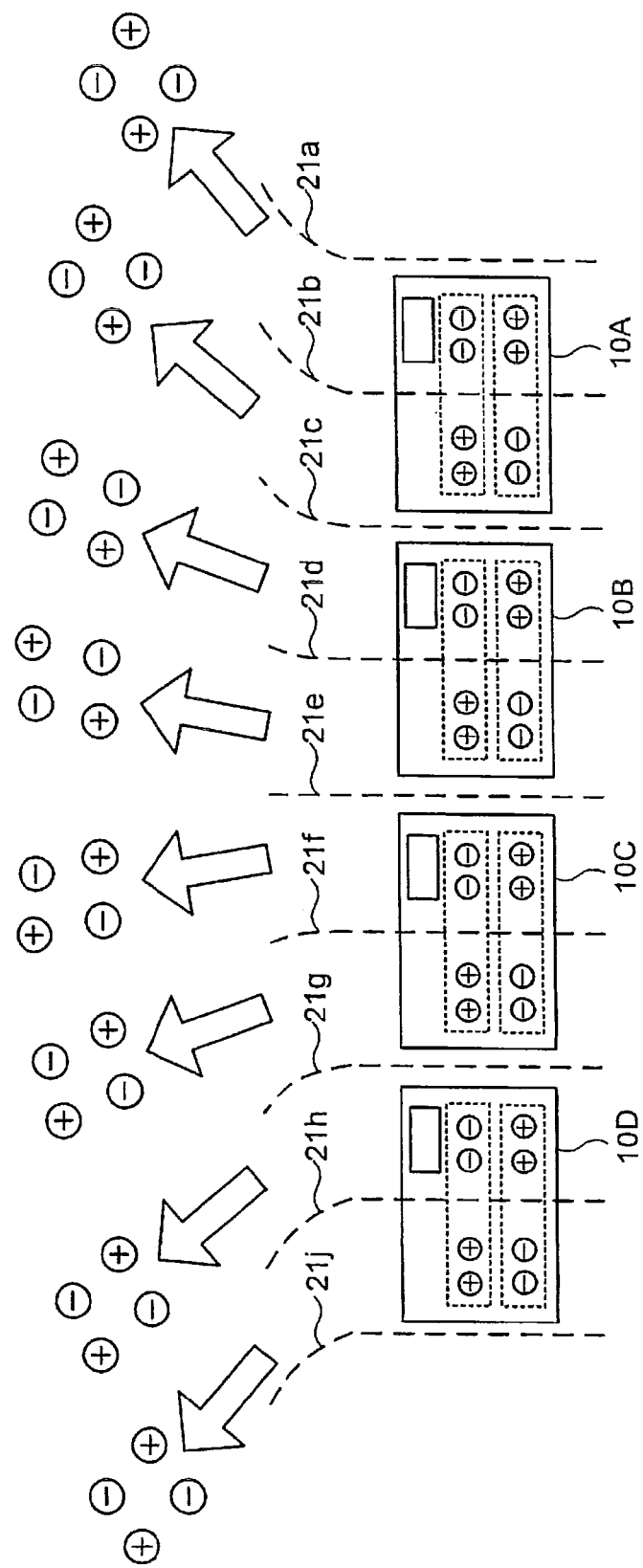
FIG. 5 is a schematic descriptive view of a flow passage.

For example, as shown in FIG. 5, the vertical wind-direction plates 21a to 21j, which partition the flow passage into the flow passages for the respective positive and negative ions generating portions of the ion generating apparatuses 10A, 10B, 10C and 10D, are disposed in such a way that the vertical wind-direction plates at the sides are more widely opened, so that it is possible to form the flow passages that exhale the ions across the wide angle.

According to the above structure, it becomes possible to send out the ions generated by the respective ion generating portions without the collision between the adjacent ions that have different polarities, so that it is possible to evenly send out the ions far into the room. However, by means of a method in which the positive and negative ions are continuously sent out via the same flow passage, it is hard to evenly mingle the positive and negative ions; and a disadvantage that the flow passage is charged with electricity is likely to happen. Because of this, in the present embodiment, ion generators, which are each of a double electrode type that disposes the two generating electrodes, that is, the positive ion generating electrode and the negative ion generating electrode close to each other, are disposed in two stages; and the ion generators are each formed as an ion generating cartridge of a two-stage ion generating type in which the polarities of the ion generating electrodes of the respective ion generators are reversed to each other. In other words, the ion generating apparatuses 10A, 10B, 10C and 10D are each formed as the ion generating cartridge type.

For example, in a case where the ion diffusing apparatus 10 having the above ion generating cartridge is operated in a living space of ten tatami mats (about 18 m$^2$), when the two-stage ion generators are alternately driven, it is experimentally confirmed that the average number of ions in the living space is 7,000/cm$^3$ or more for both of the positive ions and the negative ions. Besides, when the two-stage ion generators are driven at the same time, it is experimentally confirmed that the average number of ions is 50,000/cm$^3$ or more for both of the positive ions and the negative ions. Because of this, if the ion diffusing apparatus according to the present invention is used, it becomes possible to kill the influenza viruses and the like residing in the room in a short time.

Conventionally, it is known that the positive ions H$^+$(H$_2$O)m (m is an arbitrary integer) and the negative ions O$_2$$^-$(H$_2$O)n (n is an arbitrary integer) are sent out into the air; and floating germs and the like are killed by the reaction of the ions. However, the ions recombine with each other to disappear, so that even if it is possible to achieve a high concentration in the vicinity of an ion generating element, the longer the distance for which the ions are sent out becomes, the more rapidly the concentration decreases. Accordingly, even if it is possible to achieve an ion concentration of tens of thousands of ions per cm$^3$ in small-volume spaces such as an experimental apparatus and the like, it is possible to achieve concentrations of 2,000 to 3,000/cm$^3$ only at best in large spaces such as an actual living space, a working space and the like.

On the other hand, the inventors have discovered that at a laboratory level, when the ion concentration is 7,000/cm$^3$, it is possible to remove 99% of the bird-flu viruses in 10 minutes; and when the ion concentration is 50,000/cm$^3$, it is possible to remove 99.9% of the bird-flu viruses in 10 minutes. Both removal rates mean that if it is supposed viruses reside in the air in a concentration of 1,000/cm3, viruses remain in a concentration of 10/cm$^3$ at the 99% removal rate, and in 1/cm$^3$ at the 99.9% removal rate. In other words, by increasing the ion concentration from 7,000/cm$^3$ to 50,000/cm$^3$, the remaining viruses become 1/10. From this, it is understood that in a living space where people and the like live and a working space, for prevention of an infectious disease and for environmental cleaning, it is very important not only to send out a high concentration of ions but also to keep the high concentration throughout the spaces.

Figure 4A:
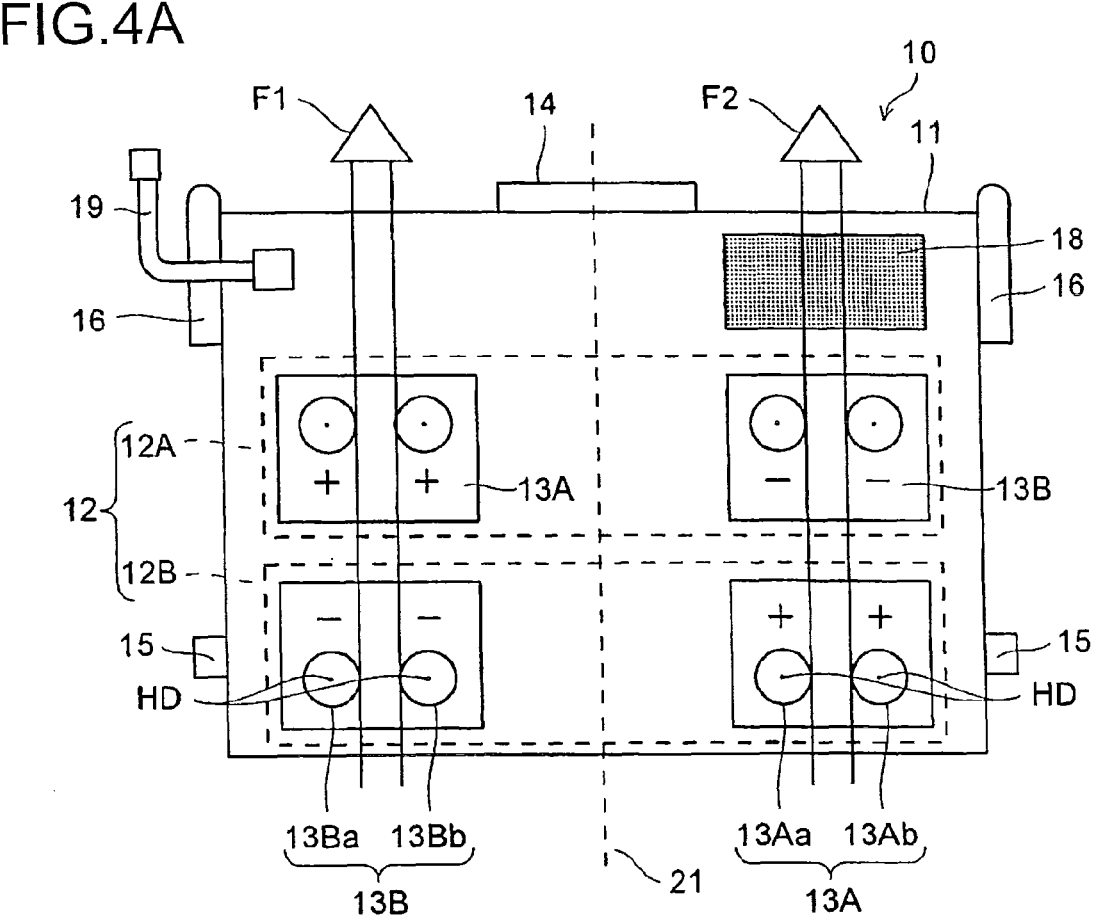
FIG. 4 shows an example of an ion generating cartridge according to the present invention, of which FIG. 4 (a) is a plan view.
Figure 4B:
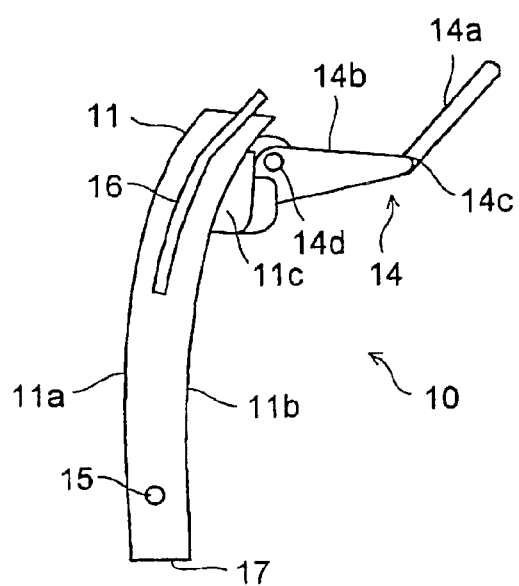

Next, the ion generating cartridge having the above structure is described by means on FIG. 4. This ion generating cartridge is the ion generating apparatus 10 formed as the cartridge type and has the same constituent members, so that the same reference numbers are used to describe the ion generating cartridge 10. The ion generating cartridge 10 shown in FIG. 4 is of the two-stage ion generating type in which an ion generator 12A including a positive ion generating portion 13A of the double electrode type and a negative ion generating portion 13B of the double electrode type; and an ion generator 12B including a negative ion generating portion 13B of the double electrode type and a positive ion generating portion 13A of the double electrode type are disposed in parallel with each other and in two stages.

The positive and negative ion generating electrodes each have a needle-shape discharge electrode HD and perform the plasma discharge between a plate-shape induction electrode around them and themselves to generate ions. Besides, if each of the discharge electrodes HD is formed as the double electrode type, the positive ion generating portion 13A includes two electrodes, that is, positive ion generating electrodes 13Aa, 13Ab; and the negative ion generating portion 13B includes two electrodes, that is, negative ion generating electrodes 13Ba, 13Bb, so that each discharge amount becomes double and it is possible to stably generate more than a predetermined amount of ions.

If a structure is employed to alternately operate the ion generators 12A, 12B of the two-stage ion generating type; and if a structure is employed to partition the flow passage by means of the vertical wind-direction plate 21, a structure is obtained, in which as the ions sent out by an air flow F1, the positive ions are sent out during a time the ion generator 12A operates; and the negative ions are sent out during a time the ion generator 12B operates.

Because of this, by setting the operation periods of the ion generator 12A and the ion generator 12B at a predetermined time interval, it is possible to intermittently exhale the positive and negative ions into the same air flow at the predetermined time intervals and to mingle both of the positive and negative ions in a predetermined concentration.

Besides, a structure is obtained, in which as the ions sent out by an air flow F2, the ion generator 12A operates to send out the negative ions; and the ion generator 12B operates to send out the positive ions. As described above, in the air flow F1 and the air flow F2, the ions having the reverse polarities are intermittently sent out; in time-dependent average, it is possible to evenly exhale the positive ions and the negative ions into the respective flow passages.

Besides, one ion generating cartridge 10 alternately operates the two ion generators 12A, 12B, so that the life of the ion generating cartridge 10 becomes double and it becomes possible to use the ion generating cartridge 10 for a long time.

The disposition position of the vertical wind-direction plate 21 that partitions the flow passage for the respective ion generating portions may be any position where it is possible to partition the flow passage for the air flow F1 and the air flow F2; if a fan that generates parallel air flows is used, it is also possible to dispose the vertical wind-direction plate 21 from the vicinity of the front end of the ion generating cartridge 10.

In the ion generating cartridge 10, the shape of a frame body 11 has a rectangular shape when viewing, from top, the ion generating surface from which the positive ion generating portion 13A and the negative ion generating portion 13B are exposed; when viewing from side, as shown in FIG. 4 (b), the ion generating surface 11a is formed into a curved surface to match with the flow surface.

Besides, the frame body 11 includes: an input-output connector portion 19 that connects with an external power supply and performs input/output of a signal; a control board that includes a high-voltage generating circuit for generating a predetermined discharge voltage from electric power obtained via the input-output connector portion, and a drive control circuit, and controls the driving of the positive ion generating electrode and the negative ion generating electrode; the ion generators 12A, 12B of the double electrode type in which the two electrodes, that is, the positive ion generating electrode and the negative ion generating electrode are disposed close to each other; and the ion sensor 18 that detects the ions generated by the ion generators.

Besides, the frame body includes: a lever member 14 that has a handle portion which is held at times of insertion and pulling-out of the cartridge and a hook portion which fixes the cartridge at a predetermined position after the insertion; on sides of the frame body 11, guide protrusion portions 15, a butt surface 17, and guide surfaces 16 that perform a guide function at the time of the cartridge insertion are disposed. The lever member 14 is rotatably disposed on a frame 11c of a rear surface 11b of the frame body 11 via a pivotal support portion 14d.

The ion sensor 18 is a negative ion detection sensor that is disposed close to the negative ion generating portion 13B of the ion generator 12A and in a downstream side with respect to the negative ion generating portion 13B; and detects the negative ions generated from the negative ion generating portion 13B. For example, it is possible to convert an ion electric current, which is output in accordance with the concentration of negative ions captured by the electrode portion that captures ions, into a voltage to detect the ions; however, this type is not limiting, and it is possible to use an ion sensor which has a function to detect that more than a predetermined amount of ions are generated.

In the ion generator 12A, the positive ion generating portion 13A always generates the positive ions, while the negative ion generating portion 13B always generates the negative ions. Besides, the predetermined positive and negative discharge voltages are applied to the respective needle-shape discharge electrodes at the same time, so that the amounts of the positive and negative ions are substantially the same as each other; by measuring the amount of either of the positive ions and the negative ions during the operation of the ion diffusing apparatus, it is possible to check whether the ion generator 12A is operating normally or not. Besides, it is possible to presume whether the ion generating cartridge 10 which unitarily includes the ion generator 12A and the ion generator 12B is normal or not. In other words, by detecting the negative ions generated from the negative ion generating portion 13B, it is possible to presume the deterioration degree of the ion generating cartridge 10 and to perform the maintenance.

Figure 3A:
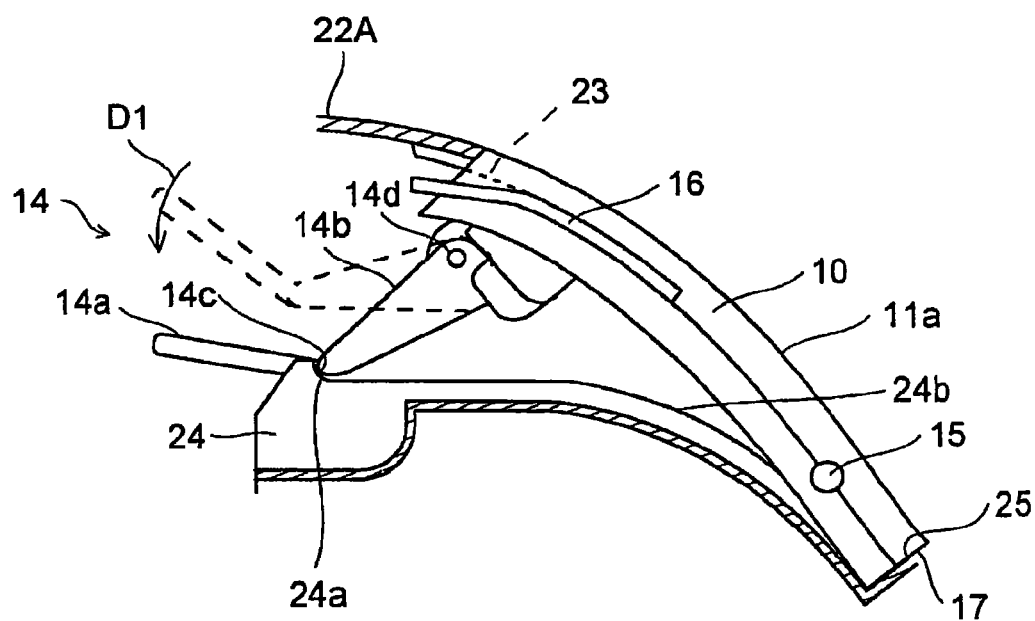
FIG. 3 is a schematic descriptive view of a lever member of an ion generating cartridge, of which FIG. 3 (a) is an enlarged descriptive view showing a fix lock portion.
Figure 3B:
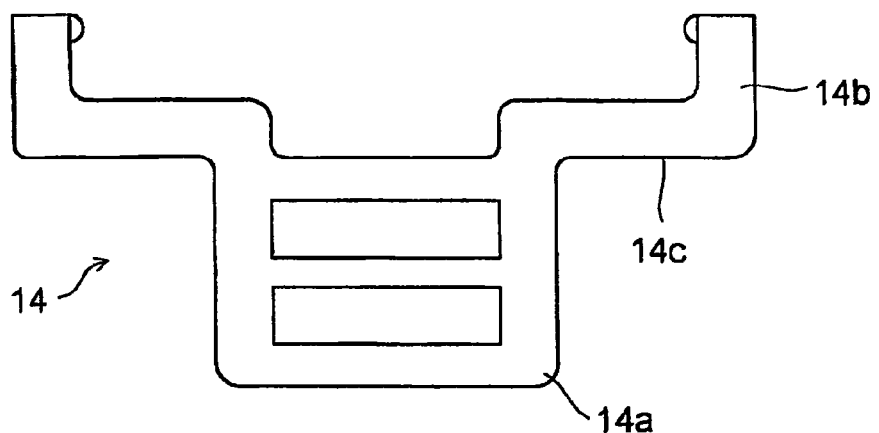

The guide protrusion portions 15 disposed on the sides of the frame body 11 of the ion generating cartridge 10 are insertion guide portions that at the insertion time of the cartridge, butt against a guide frame 24b (see FIG. 3 (a)) which forms the ion generating apparatus housing portion; with the guide protrusion portions 15 on both sides of the frame body 11 butted against the guide frames on both sides, the ion generating cartridge 10 is pushed into.

The butt surface 17 is a portion that serves as an end surface of the frame body 11 when disposing the ion generating cartridge 10 into the ion generating apparatus housing portion; and is a surface that butts against a housing portion frame 25, which forms the ion generating apparatus housing portion, to be positioned.

The guide surface 16 butts against a rear surface frame 23 of the lower lateral wind-direction plate 22A to be positioned when fixing the cartridge 10 at a predetermined position by engaging the hook portion 14c of the lever member 14 with an engagement portion 24a (see FIG. 3 (a)). As described above, the butt surface 17 for defining the insertion-end position and the guide surface 16 for defining the fix position serve as the position guide portion.

As described above, the ion generating apparatus housing portion for housing the ion generating cartridge 10 is formed at an inner place from the insertion opening 6; and is so structured as to include: the housing portion frame 25 for defining the insertion end of the cartridge; the guide frame 24b for defining the sides of the cartridge; the cut-away portion 22a from which the ion generating surface of the cartridge is exposed; the rear surface frame 23 for defining the fix position of the cartridge; and the engagement portion 24a; wherein a number of the ion generating apparatus housing portions, the number of which is equal to the number of ion generating cartridges 10, are disposed.

The lever member 14, as shown in FIG. 3 (a), is rotatably disposed on the ion generating cartridge 10 via the pivotal support portion 14d; is provided with: an arm 14b; a handle portion 14a that is held at the times of the insertion and pulling-out of the cartridge; and the hook portions 14c that engage with the engagement portions formed on the apparatus main body to fix the cartridge after the insertion. Because of this, by holding and rotating the handle portion 14a in an arrow direction D1 in the figure, it is possible to engage the hook portion 14c with the engagement portion formed on the apparatus main body.

The handle portion 14a is bent by a predetermined angle that facilitates the operation and extended from the arm 14b on which the pivotal support portion 14d is disposed. Besides, the hook portion 14c may be disposed on any portion of the lever member 14 that rotates, that is, may be disposed on the arm 14b or the handle portion 14a. In the present embodiment, as shown in FIG. 3 (b), a structure is employed, in which the handle portion 14a is extended from the arm 14b into a protrusion shape; and the arc-shape hook portions 14c that engage with the engagement portions 24a formed on the frame 24 of the apparatus main body are disposed at tip end portions of the arm 14b formed on both sides of the handle portion 14a.

Because of this, a structure is obtained, in which the hook portions 14c are formed at intermediate portions of the lever member 14: and by means of force smaller than the fit-in force between the hook portion 14c and the engagement portion 24a, it is possible to perform: the operation for holding the handle portion 14a formed at the tip end of the lever member 14, rotating the lever member 14, and engaging the hook portions 14c with the engagement portions 24a to fix the lever member 14; and the operation for disengaging the hook portion 14c from the engagement portion 24a to release the lever member 14, so that the operations become easy.

As described above, the ion generating cartridge is so structured as to include: the lever member 14 which includes the handle portion 14a that is held at the times of insertion and pulling-out of the cartridge and the hook portions 14c that fix the cartridge at the predetermined position after the insertion; the guide portions 15, the butt surface 17 and the guide surfaces 16 that are formed on the side of the frame body of the cartridge and perform the guide function at the time of the cartridge insertion, so that it is possible to obtain the ion generating apparatus of the cartridge type that is easy to insert and pull out.

Figure 2A:
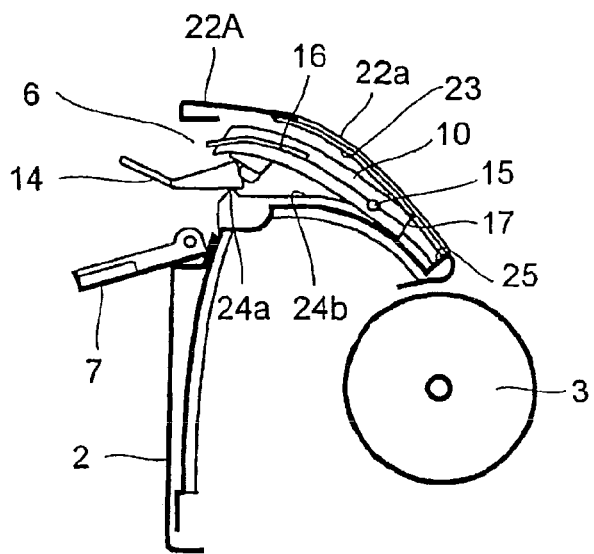
FIG. 2 is a schematic descriptive view showing an insertion procedure of an ion generating cartridge according to the present invention, of which FIG. 2 (a) is a side sectional view showing a state in which an insertion is started.
Figure 2B:
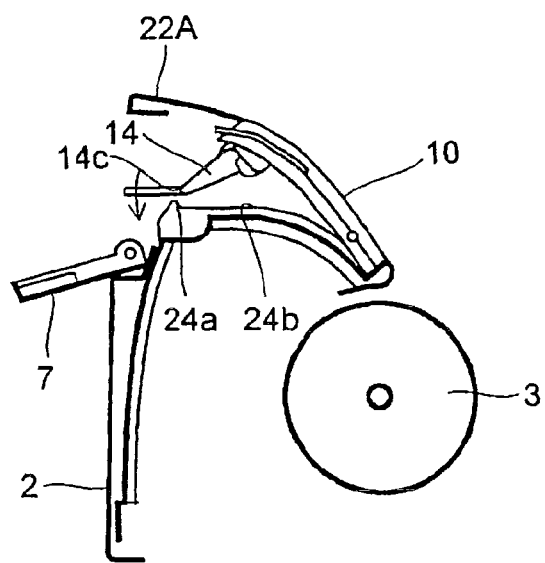
Figure 2C:
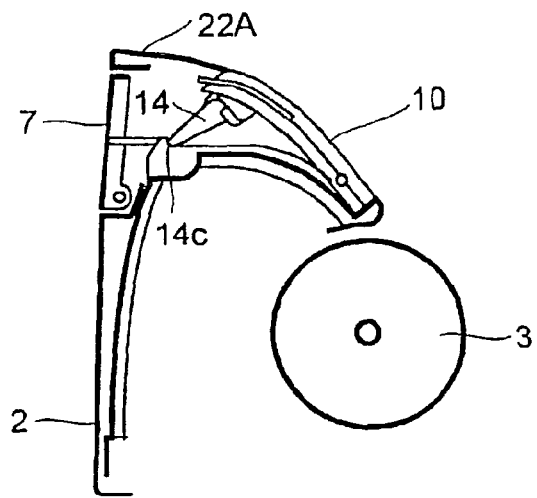

Next, a structure is described by means of FIG. 2, in which the ion generating cartridge 10 which includes the lever member 14 having the above structure is disposed in the ion diffusing apparatus 1.

As shown in FIG. 2 (a), an open-close cover 7 is opened to open the insertion opening 6; and the ion generating cartridge 10 is inserted from the opened insertion opening 6. Here, the cartridge is inserted by holding the lever member 14 as if being pushed into until the butt surface 17 butts against the housing portion frame 25. Besides, a structure is employed, in which in the time of the insertion operation, the guide protrusion portion 15 slides on the guide frame 24b.

After the ion generating cartridge 10 is pushed into until the butt surface 17 butts against the housing portion frame 25, as shown in FIG. 2 (b), the lever member 14 is pushed down to engage the hook portion 14c of the lever member 14 with the engagement portion 24a of the apparatus main body.

By means of the operation for pushing down the lever member 14 to engage the hook portion 14c with the engagement portion 24a of the apparatus main body, it is possible to fit the ion generating cartridge 10 into the cut-away portion 22a formed through the lower lateral wind-direction plate 22A. Besides, the guide surfaces 16 formed on the sides of the frame body of the ion generating cartridge 10 butt against the rear surface frame 23 of the lower lateral wind-direction plate 22A, so that the fit-in posture is defined.

When the hook portion 14c of the lever member 14 is engaged with the engagement portion 24a of the apparatus main body, as shown in FIG. 2 (c), the ion generating cartridge 10 is fixed in such a posture that the ion generating surface of the ion generating cartridge 10 is exposed via the cut-away portion 22a. This posture is a posture in which the ion generating surface is matched with the flow surface and exposed, so that it is possible to surely exhale the ions generated from the ion generating surface into the air flow.

Besides, a structure is employed, in which the in the state where the hook portion 14c of the lever member 14 is engaged with the engagement portion 24a of the apparatus main body, the opened open-close cover 7 is closable; however, as shown in FIG. 2 (a) and FIG. 2 (b), in the state where the hook portion 14c is not fixed, the open-close cover 7 interferes with the handle portion 14a of the lever member 14 when the open-close cover 7 is being closed. According to this structure, by means of the lever member 14 that is not disposed at the right position, it is possible to hinder the open-close cover 7 from being closed.

As described above, the structure is employed, in which the lever member 14 hinders the open-close cover 7 from being closed, so that it becomes possible to easily check whether the ion generating cartridge 10 is correctly disposed or not, which is preferable.

Besides, after the ion generating cartridge 10 is fixed at the predetermined position, the input-output connector portion 19 is connected to a connection terminal disposed in the apparatus main body to complete the disposition working of the ion generating cartridge 10.

The ion diffusing apparatus 1 according to the present invention has the laterally long structure to include the plurality of ion generating cartridges 10 (10A, 10B, 10C, 10D); accordingly, it is preferable that the utilised fan 3 is a crossflow fan which has a fan length to send a wind to the line in which the plurality of ion generating cartridges are disposed. A crossflow fan has high quietness, is able to be operated from a breeze range, and is preferable as a fan that is used for the ion diffusing apparatus 1 which is installed in a living room where a quiet operation is required.

Besides, as shown in FIG. 1 (a), the flow passage partitioned into the plurality of streamline flow passages is branched into: a first flow passage 4A partitioned by the lower lateral wind-direction plate 22A disposed on the inner circumference side close to the crossflow fan and the next second lateral wind-direction plate 22B; a second flow passage 4B partitioned by the second lateral wind-direction plate 22B and the next third lateral wind-direction plate 22C; a third flow passage 4C partitioned by the third lateral wind-direction plate 22C and the fourth lateral wind-direction plate 22D; and a fourth flow passage 4D partitioned by the fourth lateral wind-direction plate 22D and the upper lateral wind-direction plate 22E, so that it is possible to adjust the flow speeds in the respective flow passages and carry the ions to a distant place.

For example, it is possible to set the wind speed K1 in the first flow passage 4A on the inner circumference side at the lowest wind speed, increase gradually the wind speed K2 in the second flow passage and the wind speed K3 in the third flow passage, and set the wind speed K4 in the fourth flow passage on the outer circumference side at the fastest wind speed. According to this structure, the first flow passage 4A having the slowest wind speed carries the ions generated by the ion generating apparatus (ion generating cartridge) 10, so that the faster air flow that flows over the first flow passage 4A serves as a wall, which is able to prevent upward diffusion of the ions. Besides, the ions are carried to a distant place by means of the Coanda effect of the air flows having the faster wind speeds, so that it becomes possible to form an ion flow region having a high concentration in a lower predetermined space.

In other words, by sending out the ions into the flow passage that is one of the flow passages partitioned into the plurality of streamline flow passages and has the lowest wind speed, it becomes possible to keep the ion concentration at a high concentration in a predetermined region of the room into which the air is sent; and becomes possible to effectively remove and kill the germs in the living space where people live. Besides, it is possible to change the wind speeds in the respective flow passages by adjusting the gaps among the upper lateral wind-direction plate, the lower lateral wind-direction plate, an the intermediate wind-direction plates and by adjusting the rotation speed of the crossflow fan.

An drive start-stop operation portion 8 (see FIG. 1 (b)) for driving the ion diffusing apparatus 1 by operating the crossflow fan is disposed on the front side of the apparatus main body. In the drive start-stop operation portion 8, besides an on-off switch, it is possible to dispose, for example: an operation mode setting portion that sets the rotation speed of the crossflow fan; a cartridge disposition time setting portion that sets disposition of a new ion generating cartridge; a timer setting portion; a replacement recommendation indication portion that recommends cartridge replacement after elapse of a predetermined time after the new ion generating cartridge is disposed and the operation is started; and a level indication portion that indicates whether the amounts of the ions generated by the respective ion generating cartridges are equal to, over, or ender the predetermined amounts.

Accordingly, because the service life of the ion generating cartridge is decided in advance, by setting the disposition of a new ion generating cartridge at the time the new cartridge is disposed, it is possible to perform indication for recommending the cartridge replacement in accordance with the apparatus use time from the disposition and to notify that the replacement time is coming. Besides, if the amount of the ions generated during the apparatus use is equal to or under the predetermined amount, the information is indicated, so that it is possible to know that the maintenance of the ion generating portion is necessary.

As described above, according to the present invention, the ion generating apparatus is formed as the cartridge type in which the ion generating surface has the curved surface that matches with the flow surface of the wind-direction plate; and which unitarily includes the insertion guide portion; the position guide portion; and the lever member that engages with the engagement portion of the apparatus main body to fix the ion generating cartridge, and it is made possible to insert and pull out the cartridge from the insertion opening that is formed on the outlet side which is formed through the apparatus front side, so that it is possible to obtain the ion generating cartridge that is easy to mount and demount form the apparatus front side. Besides, the ion diffusing apparatus has the structure in which the vertical wind-direction plates for partitioning the flow passage into the flow passages for the respective positive and negative ion generating portions are disposed, so that it is possible to obtain the ion diffusing apparatus that is able to evenly send out the ions far into the room while evenly generating the positive ions and the negative ions.

Besides, the ion generating cartridge is used, which includes: the ion generator that has the positive ion generating portion and the negative ion generating portion which are of the double electrode type in which the two ion generating electrodes are disposed close to each; and the ion sensor, so that it becomes easy to handle the ion generating apparatus of the cartridge type that generates the positive and negative ions in a large amount and it is possible to easily check whether the ion generating apparatus is operating normally or not. Because of this, it is possible to obtain the ion generating cartridge that is easily replaceable.

Moreover, the ion generating cartridge is formed as the two-stage ion generating type in which the ion generators including the ion generating portions of the double-electrode type are disposed in the two stages and in parallel with each other while the polarities of the ion generating electrodes of the ion generators are disposed at reversed positions, so that it is possible to exhale the positive ions and the negative ions into the same flow passage at the same time or alternately at the predetermined time intervals to mingle both ions of the positive ions and the negative ions at a predetermined concentration.

Besides, the structure is employed, in which the flow passage that extends from the fan to the outlet is partitioned into the multi-stage streamline flow passages; the lowest flow passage having the slowest wind speed is used as the streamline flow passage into which the ions are sent out; and the streamline flow passages having the faster wind speeds are formed successively, so that it is possible to form the air wall that prevents the ion diffusion and to form the predetermined space that where the ion concentration is kept. Moreover, the crossflow fan is used as the fan, so that it is possible to obtain the ion diffusing apparatus that has high quietness, is operable from a breeze range, and preferable to a living space where a quite operation is required.

Here, the target where the ion diffusing apparatus according to the present invention is not limited to a living room; and the ion diffusing apparatus may be used in rooms (e.g., waiting rooms of a station and a hospital, halls, classrooms and the like) where general people stay for some time. Besides, the ion diffusing apparatus may be used in a room which is ventilated by opening a window or by a ventilator if the ventilation rate is equal to or under a predetermined value. Besides, the ion diffusing apparatus may be used in a room which is air-conditioned by means of an air conditioner. Moreover, by disposing a plurality of the ion diffusing apparatuses according to the present embodiments away from each other, it is possible to secure a sufficient ion concentration in wide regions of spaces (e.g., lobbies of hotels, airports and the like) that are not partitioned.

INDUSTRIAL APPLICABILITY

The ion diffusing apparatus and the ion generating cartridge according to the present invention respectively become an ion diffusing apparatus that is able to keep the remaining amount of positive and negative ions in a living room at a high concentration and become an ion generating cartridge whose maintenance is easy, so that the ion generating cartridge becomes preferably applicable to an ion diffusing apparatus that secures a living room where people want to prevent disease infection.

LIST OF REFERENCE SYMBOLS 1 ion diffusing apparatus
2 apparatus main body
3 fan
4 outlet
5 inlet
6 insertion opening
7 open-close cover
8 drive start-stop operation portion
10 ion generating apparatus (ion generating cartridge)
11a ion generating surface
12 ion generator
13A positive ion generating portion
13Aa, 13Ab positive ion generating electrodes
13B negative ion generating portion
13Ba, 13Bb negative ion generating electrodes
14 lever member
14a handle portion
14c hook portion
15 guide protrusion portion
16 guide surface
17 butt surface
18 ion sensor
19 input-output connector portion
21 vertical wind-direction plate
22 lateral wind-direction plate
22A lower lateral wind-direction plate
22E upper lateral wind-direction plate

The invention claimed is:

1. An ion diffusing apparatus that diffuses positive ions and negative ions generated by plasma discharge into a room, the ion diffusing apparatus comprises:
a fan that generates an air flow for exhaling air, which is inhaled from an inlet, from an outlet into the room via a flow passage that is formed in the apparatus;
an ion generating apparatus that includes a positive ion generating portion and a negative ion generating portion; and supplies positive ions generated from the positive ion generating portion and negative ions generated from the negative ion generating portion into the air flowing through the flow passage; and
an ion generating apparatus housing portion that houses the ion generating apparatus so that an ion generating surface of the ion generating apparatus matches with a flow surface of the ion generating apparatus which is composed of a lower lateral wind-direction plate that forms a lower wall surface of the flow passage, exposing the ion generating surface to the flow passage surface to form a portion of the flow surface; wherein
the ion generating apparatus is able to be inserted and pulled out from an insertion opening that is formed through a side of the outlet, the ion generating apparatus is formed as an ion generating cartridge that includes an ion generator that has the positive ion generating portion and the negative ion generating portion, the ion generating cartridge houses the ion generator and unitarily includes:
an insertion guide portion;
a position guide portion; and a lever member that engages with an engagement portion disposed in the ion generating apparatus housing portion of the apparatus main body to fix the position of the cartridge;

wherein a structure is employed, in which the ion generating apparatus is inserted from the insertion opening into the ion generating apparatus housing portion via the insertion guide portion and the position guide portion; and fixes the ion generating apparatus in such a posture that the ion generating surface is matched with the flow passage via the position guide portion and the lever member, and the ion generating cartridge is freely mountable and demountable into and from the ion generating apparatus housing portion.

2. The ion diffusing apparatus according to claim 1, wherein
the ion generating apparatus includes the ion generator in which the positive ion generating portion and the negative ion generating portion are spaced apart in a direction that intersects an air flow direction; and
a vertical wind-direction plate, which partitions the flow passage into flow passages for the respective positive ion generating portion and negative ion generating portion, is disposed in the flow passage.

3. The ion diffusing apparatus according to claim 2, wherein
an intermediate lateral wind-direction plate, which partitions a flow passage between the lower lateral wind-direction plate and an upper lateral wind-direction plate that forms an upper wall surface of the flow passage, is disposed to partition the flow passage that extends from the fan to the outlet into multi-stage streamline flow passages;
a plurality of the ion generating apparatuses are disposed in parallel with each other to form a continuous-length ion generating surface that has alternately the positive ion generating portion and the negative ion generating portion in a line at a predetermined pitch along the flow passage of the lower lateral wind-direction plate; and
the vertical wind-direction plate, which partitions the flow passage into the flow passages for the respective positive ion generating portion and negative ion generating portion, is so disposed as to penetrate the multi-stage streamline flow passages.

4. The ion diffusing apparatus according to claim 3, wherein each vertical wind-direction plate is angled in such a way that the ions are exhaled at a wide angle with respect to a width direction in which the ion generating apparatuses are disposed in parallel with each other.

5. The ion diffusing apparatus according to claim 1, wherein the ion generating cartridge includes:
an input-output connector portion that performs input and output;
a control board that includes a high-voltage generating circuit for generating a predetermined discharge voltage from electric power obtained via the input-output connector portion, and a drive control circuit, and controls driving of the positive ion generating portion and the negative ion generating portion by means of electric power obtained via the input-output connector portion; and
an ion sensor that detects the ions generated by the ion generating portion.

6. The ion diffusing apparatus according to claim 5, wherein the ion sensor is a negative ion detection sensor that is disposed on a downwind side with respect to the negative ion generating portion of the ion generating cartridge.

7. The ion diffusing apparatus according to claim 1, wherein a positive ion generating electrode of the positive ion generating portion of the ion generator and a negative ion generating electrode of the negative ion generating portion of the ion generator are each of a double electrode type in which two generating electrodes are disposed close to each other.

8. The ion diffusing apparatus according to claim 7, wherein the ion generating cartridge is formed as a two-stage ion generating type in which the ion generators are disposed in two stages and in parallel with each other; and positive and negative polarities of the positive ion generating electrode and the negative ion generating electrode of the respective ion generators are disposed at reversed positions.

9. The ion diffusing apparatus according to claim 8, wherein the ion generators in the respective stages of the ion generating cartridge of the two-stage ion generating type are alternately operated.

10. The ion diffusing apparatus according to claim 1, wherein an open-close cover for closing and opening the insertion opening is disposed; the ion generating cartridge is inserted until a predetermined position; when the lever member is rotated to a fix lock position where a hook portion of the lever member is engaged with the engagement portion of the main body, the closing of the open-close cover is possible; and in a state in which the lever member is not rotated to the fix lock position, the lever member hinders the open-close cover from being closed.

11. The ion diffusing apparatus according to claim 1, wherein a drive start-stop operation portion is disposed on the apparatus main body; the operation portion is provided with: a drive mode set portion that sets a rotation speed of the fan; a cartridge disposition time set portion that sets disposition of a new ion generating cartridge; a timer set portion; a replacement recommendation indication portion that recommends cartridge replacement after elapse of a predetermined time after the new cartridge is disposed and the operation is started; and a level indication portion that indicates whether the amount of the ions generated by each ion generating cartridge is equal to, over or under a predetermined amount.

12. An ion generating apparatus that generates positive ions and negative ions by means of plasma discharge, the ion generating apparatus is an ion generating cartridge comprising:
an input-output connector portion that performs input and output of a signal;
a control board that includes a high-voltage generating circuit for generating a predetermined discharge voltage from electric power obtained via the input-output connector portion, and a drive control circuit, and controls driving of the positive ion generating electrode and the negative ion generating electrode;
an ion generator which includes an ion generator of double electrode type in which two electrodes of a positive ion generating electrode and a negative ion generating electrode are disposed close to each other; and
an ion sensor that detects the ions generated by the ion generator;
the ion generating cartridge houses the ion generator and unitarily includes:
an insertion guide portion;
a position guide portion; and
a lever member that engages with an engagement portion of a main body of the apparatus to fix a position of the cartridge.

13. The ion generating cartridge according to claim 12, wherein the ion sensor is a negative ion detection sensor that detects the negative ions generated from the negative ion generating electrode.

14. The ion generating cartridge according to claim 12, wherein
- a lever member has: a handle portion that is held at times of insertion and pulling-out of the cartridge; and a hook member that fixes the cartridge in a predetermined position after the insertion; wherein
- a side portion of a frame body of the cartridge is provided with: a guide protrusion portion as the insertion guide portion that performs a guide function at the time of inserting the cartridge, a butt surface and a guide surface as the position guide portion.

15. The ion generating cartridge according to claim 12, wherein
- the ion generating cartridge has a rectangular shape when viewing an ion generating surface, from top, on which the positive and negative ion generating portions are disposed;
- the ion generator is formed as a two-stage ion generating type in which positive and negative polarities of the ion generating electrode portions are disposed at reversed positions in two stages and in parallel with each other; and
- the ion generating surface is formed into a curved surface that matches with a flow surface where the ion generating cartridge is disposed.

16. The ion generating cartridge according to claim 15, wherein the respective stages of the ion generator of the two-stage ion generating type are alternately operated.

\* \* \* \* \*